(12) United States Patent
McKelvey et al.

(10) Patent No.: US 8,003,672 B2
(45) Date of Patent: Aug. 23, 2011

(54) CB-1 RECEPTOR MODULATOR FORMULATIONS

(75) Inventors: Craig McKelvey, Ambler, PA (US); Sarah Geers, Newark, NJ (US); Justin Moser, Collegeville, PA (US); Bhagwant Rege, Collegeville, PA (US); Dina Zhang, Watchung, NJ (US); Sutthilug Sotthivirat, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 89 days.

(21) Appl. No.: 12/386,402

(22) Filed: Apr. 17, 2009

(65) Prior Publication Data

US 2009/0264436 A1    Oct. 22, 2009

Related U.S. Application Data

(60) Provisional application No. 61/124,946, filed on Apr. 21, 2008.

(51) Int. Cl.
  *A61K 31/44* (2006.01)
(52) U.S. Cl. ........ 514/351; 514/345; 514/277; 514/183; 546/300; 546/290; 424/486
(58) Field of Classification Search ........................ None
  See application file for complete search history.

(56) References Cited

U.S. PATENT DOCUMENTS

| | | | |
|---|---|---|---|
| 6,699,871 B2 | 3/2004 | Edmondson et al. | |
| 7,326,708 B2 | 2/2008 | Cypes et al. | |
| 2005/0008706 A1* | 1/2005 | Holm et al. | 424/489 |
| 2007/0104741 A1* | 5/2007 | Murty et al. | 424/400 |

FOREIGN PATENT DOCUMENTS

| | | |
|---|---|---|
| WO | WO03/077847 A2 | 9/2003 |
| WO | WO03/077847 A3 | 9/2003 |
| WO | WO2006/119260 A2 | 11/2006 |
| WO | WO2006/119260 A3 | 11/2006 |

OTHER PUBLICATIONS

STN Registry record for taranabant (Jul. 2004).*
"The mechanisms of drug release from solid dispersions in water-soluble polymers" by Craig, Int. J. Pharmaceut. 231, 131-44 (2002).*
"Solid Dispersion of Poorly Water-Soluble Drugs: Early Promises, Subsequent Problems, and Recent Breakthroughs" by Serajuddin, J. Pharm. Sci. 88, 1058-66 (1999).*
"Drug delivery strategies for poorly water-soluble drugs" by Fahr et al., Expert Opin. Drug Deliv. 4, 403-16 (2007).*
"Improving drug solubility for oral delivery using solid dispersions" by Leuner et al., Eur. J. Pharmaceut. Biopharm. 50, 47-60 (2000).*
"Solid dispersions as strategy to improve oral bioavailability of poor water soluble drugs" by Vasconcelos et al., Drug Discovery Today 12, 1068-75 (2007).*

* cited by examiner

*Primary Examiner* — Anish Gupta
*Assistant Examiner* — Theodore R West
(74) *Attorney, Agent, or Firm* — Janet E. Fair; John C. Todaro

(57) ABSTRACT

Described herein are solid, stable pharmaceutical formulations of cannabinoid receptor inverse agonists, such as taranabant, and processes of making such formulations. Additionally, described herein are solid stable pharmaceutical formulations of cannabiniod inverse agonists, such as taranabant, and an additional therapeutic agent, as well as processes for making such pharmaceutical formulations.

15 Claims, 2 Drawing Sheets

CB-1 RECEPTOR MODULATOR FORMULATIONS

CROSS-REFERENCE TO RELATED APPLICATIONS

This application is related to U.S. Provisional Application Ser. No. 61/124,946, filed Apr. 21, 2008, the contents of which are hereby incorporated by reference.

BACKGROUND

Since the mid-seventies, the prevalence of obesity among adults has increased sharply. Data from two National Health and Nutrition Examination Surveys show that among adults 20-74 years of age the prevalence of obesity increased from 15.0% (in the 1976-1980 survey) to 32.9% (in the 2003-2004 survey).

Obesity and certain conditions associated with obesity, such as diabetes, are often treated by encouraging patients to lose weight by reducing their caloric intake or by increasing their level of physical activity. However, for many individuals, maintaining a reduced calorie diet and an exercise regime is difficult, and often such treatment results in poor patient compliance. For many individuals weight loss drugs can serve as a successful treatment in conjunction with, or as an alternative to diet and exercise. However, certain currently available weight loss drugs, which include orlistat [Davidson, M. H. et al., *JAMA*, 281: 235-42 (1999)], effect weight loss by preventing lipid absorption by the body and, as a result, are limited by gastrointestinal side effects.

Recently, cannabinoid 1 (CB-1) receptor modulators, such as rimonabant, which is sold as ACOMPLIA in many countries, have been found to effect weight loss by targeting receptors in the brain linked to appetite. Since CB-1 receptor modulators effect weight loss through a different mechanism than that of orlistat, CB-1 receptor modulators are not limited by the same gastrointestinal side effects.

One promising weight loss drug is CB-1 receptor inverse agonist, taranabant, which is further described in WO2003/077847, which is incorporated herein by reference in its entirety. Taranabant, however, is insoluble in aqueous solution, making processing and manufacturing an issue. Therefore, there exists a need for stable, solid pharmaceutical formulations, and processes for making such formulations, that include water insoluble drugs, such as taranabant.

Additionally, it is quite common that effective treatment of an obese individual may not only include treating the obesity but also treating any conditions associated with obesity that the individual may also be suffering from. Conditions associated with obesity include, but are not limited to diabetes; hypertension; elevated plasma insulin concentrations; insulin resistance; dyslipidemia; hyperlipidemia; endometrial, breast, prostate, kidney and colon cancer; osteoarthritis; respiratory complications, such as obstructive sleep apnea; gallstones; atherosclerosis; heart disease; abnormal heart rhythms; and heart arrhythmias (Kopelman, P. G., Nature, 404: 635-643 (2000)). Therefore, there is also a need for stable pharmaceutical formulations, and processes of making such formulations, that can include water insoluble drugs, such as taranabant, and other therapeutic agents. Certain combinations of taranabant and other therapeutic agents are described in WO 2006/119260, which is incorporated by reference in its entirety.

However, processing and manufacturing single dosage forms that contain a water insoluble therapeutic agent, such as taranabant, and an additional therapeutic agent, such as a water soluble therapeutic agent, is difficult. Generally, water insoluble therapeutic agents are formulated into liquid dosage forms, such as liquid-filled capsules, using lipids. Adding a water soluble therapeutic agent to such a formulation is problematic due to the fact that the water soluble drug may have solubility or stability issues when introduced into the liquid lipid formulation. Thus, there is not only a need for stable pharmaceutical formulations that can include water insoluble drugs, such as taranabant, and other therapeutic agents, but there is a need for stable, solid pharmaceutical formulations and processes of making such formulations that can include water insoluble drugs, such as taranabant, and water soluble therapeutic agents that can be formed into solid, oral single fixed dosage forms. Also there is a need for such pharmaceutical formulations to improve the bioavailability of one or both of the therapeutic agents or at least result in equivalent bioavailability of one or both of the therapeutic agents compared to separate administration of each of the therapeutic agents.

SUMMARY

Described herein are solid, stable pharmaceutical formulations of cannabinoid modulators, and processes of making such formulations. Additionally, described herein are solid, stable pharmaceutical formulations of cannabiniod modulators and an additional therapeutic agent, as well as, processes for making such pharmaceutical formulations. In certain embodiments, the solid pharmaceutical formulations described herein include a CB-1 receptor inverse agonist, such as taranabant, and a polymer.

In some embodiments, the pharmaceutical formulations described herein include a solid dispersion of a CB-1 receptor inverse agonist, such as taranabant and a polymer. The solid dispersions are capable of providing enhanced physical and chemical stability. Solid dispersions can also improve bioavailability of the CB-1 inverse agonist compared to CB-1 receptor inverse agonist pharmaceutical formulations that do not include solid dispersions.

In certain embodiments, the pharmaceutical formulations described herein, include a solid dispersion of taranabant and a concentration-enhancing polymer. For example, the pharmaceutical compositions described herein can include a solid dispersion of taranabant and polyvinylpyrrolidinone-polyvinyl acetate (PVP-PVA) copolymer.

DETAILED DESCRIPTION

Definitions

Figure 1:
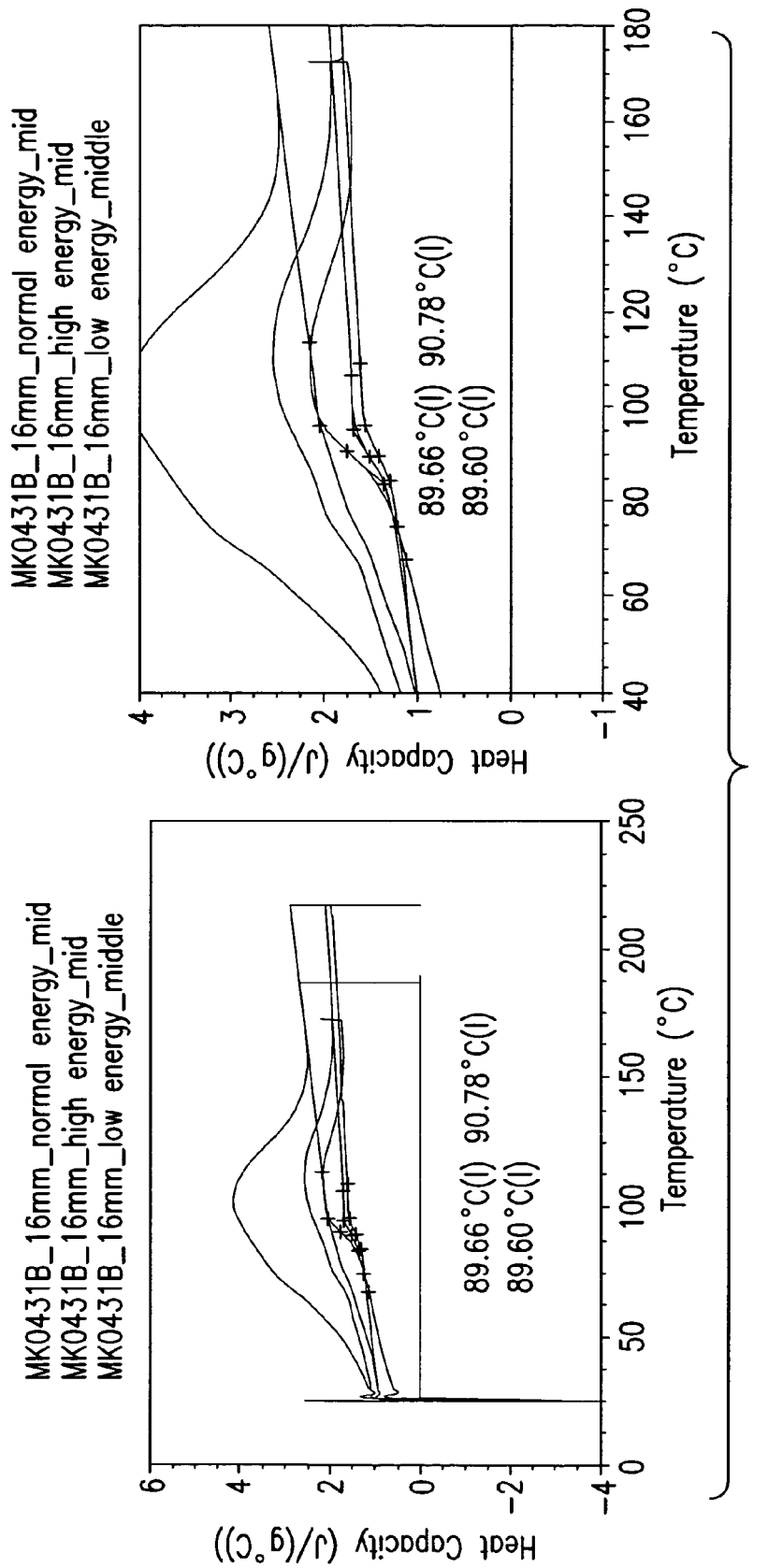
FIG. 1 shows cyclic differential scanning calorimetry (DSC) of extrudate sample of Formula 1 of Example 1 from the 16 mm extruder.

As used herein, the term "amorphous" refers to material sample(s) having no apparent crystalline form which can be detected by conventional methods, such as X-ray crystallography.

As used herein, the phrase "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. Degree of substitution refers to the average number of the three hydroxyls per saccharide repeat unit on the cellulose chain that have been substituted. For example, if all of the hydroxyls on the cellulose chain have been phthalate substituted, the phthalate degree of substitution is 3.

As used herein, the phrase "concentration-enhancing polymers" refers to polymers that are capable of forming solid dispersions, such as amorphous solid dispersions with therapeutic agents that are insoluble or almost completely insoluble in water by (a) dissolving the therapeutic agent or (b) interacting with the therapeutic agent in such a way that the therapeutic agent does not form crystals or crystalline domains in the polymer, or does not form long-range crystalline structures.

As used herein the term "diabetes," includes both insulin-dependent diabetes mellitus (i.e., IDDM, also known as Type 1 diabetes) and non-insulin-dependent diabetes mellitus (i.e., NIDDM, also known as Type 2 diabetes) and is characterized by a fasting plasma glucose level of greater than or equal to 126 mg/dl.

As used herein, the term "HPMCAS" can refer to a family of cellulose derivatives that can have (1) two types of ether substituents, methyl and/or 2-hydroxypropyl and (2) two types of ester substituents, acetyl and/or succinyl. It is referred to in scientific literature as O-(2-hydroxypropyl)-O-methyl-cellulose acetate succinate. The degree of substitution for each of the four general types just noted can be varied over a wide range to affect the chemical and physical properties of the polymer.

As used herein the phrase "surfactant" refers to a molecule with surface active properties.

As used herein the phrase "solid dispersion" refers to the dispersion of one or more therapeutic agents in an inert carrier or matrix at solid state. The phrase "solid dispersion" does not include simple mixtures. There are many categories of solid dispersions, including eutectic mixtures, solid solutions, glass solutions of suspension, compound or complex formations between the therapeutic agent and the carrier, amorphous precipitations of a therapeutic agent in a crystalline carrier and any combination of the aforementioned groups. In certain embodiments described herein, the solid dispersions are amorphous. In other embodiments described herein, the solid dispersions include some crystalline structure, for example solid dispersion without long-range crystalline order.

As used herein the term "obesity" refers to a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a BMI greater than or equal to 30 $kg/m^2$, or a condition whereby a subject with at least one co-morbidity has a BMI greater than or equal to 27 $kg/m^2$. An "obese subject" is an otherwise healthy subject with a BMI greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower BMI in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asian countries, a "subject at risk of obesity" is a subject with a BMI of greater than 23 $kg/m^2$ to less than 25 $kg/m^2$.

The terms "prevent(s)", "prevented", "preventing" or "prevention" are used herein interchangeably and refer to any prevention or any contribution to the prevention of a condition in an animal or the development of a condition if none has occurred in an animal which may be predisposed to such condition but has not yet been inflicted with or diagnosed as having such condition.

As used herein the terms "subject(s)", "individual(s)" and "patient(s)" can be used interchangeably and refer to a mammal, preferably a human, who has been the object of treatment, observation or experiment. In one embodiment the term "mammal" is a "human" said human being either male or female. The instant combinations are also useful for treating or preventing obesity and obesity-related conditions in cats and dogs. As such, the term "mammal" includes companion animals such as cats and dogs.

As used herein the phrase "subject in need thereof" refers to a subject who is in need of treatment or prophylaxis as determined by a researcher, veterinarian, medical doctor or other clinician. In one embodiment, a subject in need thereof is a mammal. In another embodiment, a subject in need thereof is a human. In another yet embodiment, a subject in need thereof is an obese subject. In another embodiment, a subject in need thereof is an obese subject with diabetes. In another embodiment, a subject in need thereof is an obese subject at risk of developing diabetes. In another embodiment, a subject in need thereof is an obese diabetic subject. In another embodiment, a subject in need thereof is a diabetic subject at risk of developing obesity. In another embodiment, a subject in need thereof is an obese subject with cardiac hypertrophy, or left ventricular hypertrophy. In another embodiment, a subject in need thereof is an obese diabetic subject with cardiac hypertrophy, or left ventricular hypertrophy. In another embodiment, a subject in need thereof is an obese subject at risk of developing cardiac hypertrophy, or left ventricular hypertrophy.

As used herein the phrase "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

The pharmaceutically acceptable salts of the pharmaceutical formulations described herein include formulations wherein one of the individual components of the formulation is in the form of a pharmaceutically acceptable salt, or formulations wherein some or all of the individual components are in the form of pharmaceutically acceptable salts (wherein the salts for each of the components can be the same or different), or a pharmaceutically acceptable salt of the combined components (i.e., a salt of the composition).

The terms "treat(s)", "treated", "treating" or "treatment" are used herein interchangeably and refer to any treatment of a condition in an animal, such as a human, diagnosed or inflicted with such condition and includes, but is not limited to: (a) caring for an animal diagnosed or inflicted with a condition; (b) curing or healing an animal diagnosed or inflicted with a condition; (c) causing regression of a condition in an animal; (d) arresting further development or progression of a condition in an animal; (e) slowing the course of a condition in an animal; (f) relieving, improving, decreasing or stopping symptoms a condition in a animal; (g) relieving, decreasing or stopping the symptoms caused by or associated with a condition in an animal; or (h) reducing the frequency, number or severity of episodes caused by or associated with a condition in an animal.

Pharmaceutical Formulations
Cannabinoid Receptor Modulators

The pharmaceutical formulations described herein include modulators of the cannabinoid-1 (CB-1) receptor. Modulators of the CB-1 receptor, such as antagonists or inverse agonists of the CB-1 receptor, can be useful in the treatment, prevention and suppression of conditions mediated by the CB-1 receptor. For example the antagonists or inverse agonists of the CB-1 receptor described in WO2003/077847, which is incorporated by reference in its entirety, are useful as centrally acting drugs in the treatment of psychosis, memory deficits, cognitive disorders, migraine, neuropathy, neuroinflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. CB-1 receptor modulators can also be useful for the treatment of substance abuse disorders, particularly to opiates, alcohol, marijuana, and nicotine and for the treatment of constipation and chronic intestinal pseudo-obstruction, as well as for the treatment of asthma, and cirrhosis of the liver.

The CB-1 receptor modulators described in WO2003/077847 are also useful for the treatment of eating disorders by inhibiting excessive food intake and the resulting obesity and complications associated therewith.

In certain embodiments, the pharmaceutical formulations described herein include the CB-1 receptor inverse agonist, taranabant, or a pharmaceutically acceptable salt thereof. Taranabant is represented by the following chemical structure:

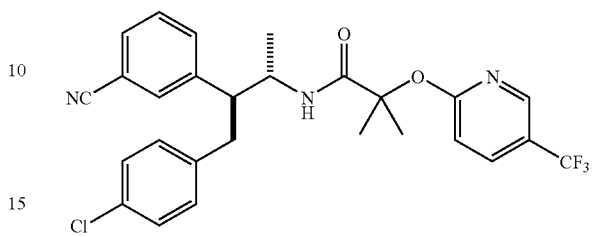

and is further described in WO 2003/077847. Methods of making taranabant are also described in WO 2003/077847.

The structure of the active metabolite of taranabant is as follows:

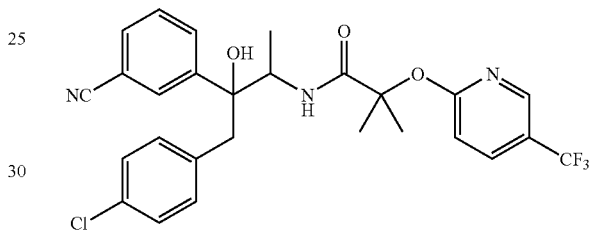

Thus, the pharmaceutical formulations described herein include a solid dispersion of a cannabinoid receptor inverse agonist having formula I:

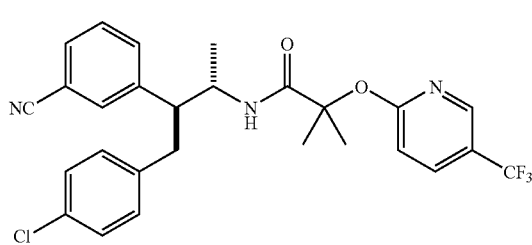

and a concentration-enhancing polymer. In such embodiments, taranabant can be 1% to 20% by weight of the solid dispersion. In certain embodiments, the pharmaceutical formulations described herein include 1%, 2%, 3%, 4%, 5%, 6%, 7%, 8%, 9%, 10%, 11%, 12%, 13%, 14%, 15%, 16%, 17%, 18%, 19% or 20% of taranabant by weight of the solid dispersion. In still other embodiments, the pharmaceutical formulations described herein include 0.5%, 1.5%, 2.5%, 3.5%, 4.5%, 5.5%, 6.5%, 7.5%, 8.5%, 9.5%, 10.5%, 11.5%, 12.5%, 13.5%, 14.5%, 15.5%, 16.5%, 17.5%, 18.5% or 19.5% of taranabant by weight of the solid dispersion.

Polymers

The pharmaceutical formulations described herein include a CB-1 receptor modulator, such as taranabant or a pharmaceutically acceptable salt thereof, and a polymer. Suitable polymers include polymers that are capable of forming solid dispersions with a CB-1 receptor modulator, such as taranabant. Such polymers include concentration-enhancing polymers. Suitable concentration-enhancing polymers are polymers that are capable of forming solid dispersions, such as amorphous dispersions, with taranabant by (a) dissolving taranabant or (b) interacting with taranabant in such a way that the taranabant does not form crystals or crystalline domains in the polymer, or does not form long-range crystalline structures. Concentration-enhancing polymers can be water soluble or readily dispersible in water, so that when the polymer is placed in water or an aqueous environment (e.g. fluids in the gastrointestinal (GI) tract or simulated GI fluids), the solubility and/or bioavailability of taranabant is increased when compared to the solubility or bioavailability of taranabant in absence of the polymer.

It should be noted that the term "polymer" is intended to include blends of polymers in addition to a single species of polymer. Thus, when specific polymers that are suitable for use in the formulations described herein are blended, the blends of such polymers may also be suitable.

Suitable polymers that can be used with the pharmaceutical formulations described herein include, non-cellulosic, non-ionic polymers such as, vinyl polymers and copolymers having substituents that are hydroxy, alkyl, acyloxy, and cyclic amides. These include polyvinyl alcohols that have at least a portion of their repeat units in the unhydrolyzed (vinyl acetate) form (e.g. polyvinyl alcohol-polyvinyl acetate copolymers); polyvinyl pyrrolidinone; polyethylene polyvinyl alcohol copolymers; and polyvinylpyrrolidinone-polyvinyl acetate copolymers. Of special interest are polyvinylpyrrolidinone and polyvinylpyrrolidinone copolymers, such as polyvinylpyrrolidinone-polyvinyl acetate copolymers, available as KOLLIDON polymers and copolymers. A representative copolymer is KOLLIDON VA64 (copovidone).

Suitable polymers for use with the pharmaceutical formulations described herein, also include ionizable, non-cellulosic polymers. Examples include, but are not limited to, carboxylic acid functionalized vinyl polymers, such as the carboxylic acid functionalized polymethacrylates and carboxylic acid functionalized polyacrylates, such as the EUDRAGITS copolymers; amine-functionalized polyacrylates and polymethacrylates; proteins; and carboxylic acid functionalized starches such as starch glycolate.

Additionally, suitable polymers can include amphiphilic polymers, such as amphiphilic polymers that are block copolymers of ethylene oxide (or glycol) and propylene oxide (or glycol), where the poly(propylene glycol) oligomer units are relatively hydrophobic and the poly(ethylene glycol) units are relatively hydrophilic.

Other suitable polymers include neutral and ionizable cellulosic polymers. Neutral cellulosic polymers include polymers that are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxyalkyl groups such as hydroxymethyl, hydroxyethyl, hydroxypropyl, etc.; and aryl groups such as phenyl. Examples of ester-linked non-ionizable groups include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Examples of non-ionizable cellulose polymers that may be used in the pharmaceutical formulations described herein include, but are not limited to, hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose. Additionally, a preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

Cellulosic polymers that are at least partially ionizable at physiologically relevant pH and include at least one ionizable substituent, which may be either ether-linked or ester-linked are also suitable for use in the pharmaceutical formulations described herein. Examples of ether-linked ionizable substituents include, but are not limited to, carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid, such as ethoxynicotinic acid, and the various isomers of picolinic acid such as ethoxypicolinic acid, etc.; thiocarboxylic acids, such as 5 thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary-ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as aminosalicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer water soluble at least at pH values where any ionizable groups are ionized. In some cases, the aromatic group may itself be ionizable, such as phthalate or trimellitate substituents.

Examples of cellulosic polymers that are at least partially ionized at physiologically relevant pH include, but are not limited to, hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethylethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose trimellityl, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Cellulosic ionizable polymers that possess both a carboxylic acid functional aromatic substituent and an alkylate substituent and thus are amphiphilic, are also suitable for use in the pharmaceutical formulations described herein. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

In certain embodiments polymers included in the pharmaceutical formulations described herein include, but are not limited to, polyvinylpyrrolidone (PVP), copolymers of PVP, such as vinyl acetate, hydroxypropyl methyl cellulose (HPMC), hydroxypropyl cellulose (HPC), hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, carboxymethylethyl cellulose, hydroxypropyl cellulose acetate trimellitate, hydroxypropyl cellulose acetate phthalate, cellulose acetate terephthalate, cellulose acetate isophthalate and polyethylene glycol (PEG), polymethacrylates and poly lactic co-glycolic acid (PLGA). Preferred polymers include, but are not limited to, PVP and copolymers thereof such as polyvinylpyrrolidinone-polyvinyl acetate (PVP-PVA).

The pharmaceutical formulations described herein can include 2% to 98% of polymer by weight. In certain embodiments, the pharmaceutical formulations described herein include 5%, 10%, 15%, 20%, 25%, 30%, 35%, 40%, 45%, 50%, 55%, 60%, 65%, 70%, 75%, 80%, 85%, 90% or 95% of polymer by weight. In certain embodiments described herein pharmaceutical formulations include a solid dispersion that includes 70%, 75%, 80%, 85%, 90% or 95% of polymer by weight. In certain embodiments described herein pharmaceutical formulations include a solid dispersion that includes 85% to 90% of PVP-PVA by weight. For example, in one embodiment the pharmaceutical formulations described herein include a solid dispersion that includes 85% of PVP-PVA by weight. In another embodiment, the pharmaceutical formulations described herein include a solid dispersion that includes 87% of PVP-PVA by weight.

Surfactants

The pharmaceutical formulations described herein can also include one or more surfactants. In certain embodiments the surfactants are included in the solid dispersion, however in other embodiments one or more surfactants can be included in the pharmaceutical formulations described herein but not included in the solid dispersions. In certain embodiments described herein, the solid dispersion that includes a CB-1 modulator and a polymer can further include one or more surfactants. The surfactants can increase the rate of dissolution by facilitating wetting, thereby increasing the maximum concentration of the dissolved therapeutic agent. The surfactants may also make the dispersion easier to process. Surfactants may also stabilize the dispersions by inhibiting crystallization or precipitation of the therapeutic agent by interacting with the dissolved therapeutic agent by such mechanisms such as, complexation, formation of inclusion complexes, formation of micelles, and adsorption to the surface of the therapeutic agent.

Suitable surfactants include cationic, anionic, and nonionic surfactants. These include for example fatty acids and alkyl sulfonates; cationic surfactants such as benzalkonium chloride, examples of which include Hyamine 1622; anionic surfactants, such as dioctyl sodium sulfosuccinate, examples of which include Docusate Sodium and sodium lauryl sulfate; sodium dodecyl sulfate; sorbitan fatty acid esters, examples of which include the SPAN series of surfactants; Vitamin E TPGS; polyoxyethylene sorbitan fatty acid esters, examples of which include the TWEEN series of surfactants; polyoxyethylene castor oils and hydrogenated castor oils such as CREMOPHOR RH-40 and CREMOPHOR EL; LIPOSORB P-20; CAPMUL POE-0; copolymers of polyethylene oxide and polypropylene oxide, including PLURONICS like Poloxamer 407; and natural surfactants such as sodium taurocholic acid, 1-palmitoyl-2-oleoyl-sn-glycero-3-phosphocholine, lecithin, and other phospholipids and mono- and diglycerides.

The pharmaceutical formulations described herein can include 0.1% to 15% of surfactant by weight. In certain embodiments, the pharmaceutical formulations described herein include 0.5%, 1%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 11.5%, 12.0%, 12.5%, 13.0%, 13.5%, 14.0%, 14.5% or 15.0% of surfactant by weight. In other embodiments, the pharmaceutical formulations described herein include solid dispersions that include 0.5%, 1%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 11.5%, 12.0%, 12.5%, 13.0%, 13.5%, 14.0%, 14.5% or 15.0% of surfactant by weight. In certain embodiments described herein pharmaceutical formulations include a solid dispersion that includes 3% to 5% of Vitamin E TPGS, TWEEN 80, SPAN 80 or a combination thereof. For example, in one embodiment the pharmaceutical formulations described herein include a solid dispersion that includes 1.5% of TWEEN 80 and 1.5% of SPAN 80 by weight. In another embodiment, the pharmaceutical formulations described herein include a solid dispersion that includes 5% of Vitamin E TPGS by weight. In still another embodiment, the pharmaceutical formulations described herein include a solid dispersion that includes 15% of poloxamer 407 by weight.

Dosage Forms and Additives

The pharmaceutical formulations described herein can be formulated into solid pharmaceutical dosage forms that can be administered orally. Oral pharmaceutical dosage forms can be in the form of individualized or multi-unit doses, such as tablets including suspension tablets, chewable tablets, rapid melt tablets, effervescent tablets; caplets; powders including effervescent powders; capsules including single or double shell gelatin capsule, tablet-filled capsules; pellets or granules.

While the embodiments described herein contemplate any solid dosage form suitable for oral administration, tablets, capsules, tablet-filled capsules and caplets are especially preferred. When the pharmaceutical compositions of the present invention are formed into tablets or caplets, it is to be understood that the tablets or caplets may be scored, and that they may be of any suitable shape and size, such as round, square, rectangular, oval, diamond, pentagon, hexagon or triangular, so long as the objectives of the present invention are not defeated. It is to be further understood that when tablet-filled capsules are selected, the tablets utilized therewith may be formed into shapes that either (a) correspond to the capsules to permit over-coating or encapsulation via the capsules or (b) readily fit inside the capsules.

When the pharmaceutical formulations described herein are formed into solid, oral pharmaceutical dosage forms, such formulations may also include pharmaceutically acceptable additives. Such additives include, but are not limited to, lactose, starch, sucrose, glucose, methyl cellulose, microcrystalline cellulose, silicified microcrystalline cellulose, anhydrous dibasic calcium phosphate, magnesium stearate, mannitol, sorbitol, croscarmellose sodium and the like. Moreover, when desired or necessary, suitable binders, lubricants, disintegrating agents, glidants, buffers, coatings, and coloring agents can also be incorporated. Suitable binders can include starch, gelatin, natural sugars such a glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Glidants include colloidal silicon dioxide, talc, and the like. Lubricants used in these dosage forms include sodium oleate, sodium stearyl fumerate, sodium stearate, magnesium stearate, sodium benzoate, sodium acetate, sodium chloride and the like. Various other materials may be present as coatings or to modify the physical form of the dosage unit. For instance, tablets may be coated with shellac, sugar or both.

For example, the pharmaceutical formulations described herein encompass a solid dispersion of taranabant and PVP-PVA combined with microcrystalline cellulose, anhydrous dibasic calcium phosphate, croscarmellose sodium, magnesium stearate and sodium strearyl fumerate. Such a pharmaceutical formulation can be formed into tablets.

In certain embodiments, the pharmaceutical formulations described herein are formed into solid oral dosage forms that include a therapeutically effective amount of a CB-1 modulator, such as taranabant, in an amount of about 0.001 mg or less to about 200 mg or more, or preferably from about 0.01 mg to about 100 mg or preferably from about 0.1 mg to about 50 mg. Preferably, the dosage range will be between about 0.5 mg to about 6 mg of a CB-1 modulator such as taranabant per patient per day.

By way of example, a particularly preferred solid oral dosage form may contain taranabant in a dosage amount of about 0.5 mg, about 1 mg, about 1.5 mg, about 2 mg, about 2.5 mg, about 3 mg, about 3.5 mg, about 4 mg, about 4.5 mg, about 5 mg, about 5.5 mg, or about 6 mg. Of particular interest are 0.5 mg to 6 mg taranabant tablets. Of course, it should be appreciated that a particular unit dosage form and amount can be selected to accommodate the desired frequency of administration used to achieve a specified daily dosage and therapeutic effect. For example, solid oral dosage forms described herein may be administered to individuals on a regimen of one, two or more doses per day, at any time of the day.

It should be noted that the dosage amount may vary from patient to patient depending upon the nature and severity of the condition, the patient's weight, special diets being followed by a patient, concurrent medication, and other factors, recognized by those skilled in the art. Based upon the foregoing, precise dosages depend on the condition of the patient and are determined by discretion of a skilled clinician.

Additional Therapeutic Agents

The pharmaceutical formulations described herein can be used in combination with additional therapeutic agents. In certain embodiments, the pharmaceutical formulations described herein and the additional therapeutic agent may be in separate dosage forms and may be administered via the same or a different route. For example, the pharmaceutical formulations described herein may be administered orally while the additional therapeutic agent is administered parenterally or, alternatively, both may be administered orally. Additionally, the pharmaceutical formulations described herein and the additional therapeutic agent may be administered contemporaneously or sequentially.

In other embodiments, the pharmaceutical formulations described herein can include the additional therapeutic agent. The pharmaceutical formulations described herein allow water insoluble therapeutic agents, such as taranabant, to be combined with water soluble therapeutic agents and formulated into a solid, oral, fixed dosage form, such as a tablet. Examples of additional therapeutic agents that may be included with the pharmaceutical formulations described herein include, but are not limited to: antipsychotic agents, cognition enhancing agents, anti-migraine agents, anti-asthmatic agents, anti-inflammatory agents, axiolytics, anti-Parkinson's agents, anti-epileptics, anorectic agents, dipeptidyl peptidase-IV (DPP-4) inhibitors, serotonin reuptake inhibitors, and other anti-obesity and anti-diabetic agents. Of special interest are anti-diabetic and other anti-obesity agents such as dipeptidyl peptidase-IV (DPP-4) inhibitors and CB-1 modulators. Suitable DPP-4 inhibitors include, sitagliptin, alogliptin, saxagliptin, denagliptin, melogliptin, vildagliptin, BI-1356 and PF-7342000.

For example, in certain embodiments the pharmaceutical formulations described herein include a solid dispersion of taranabant, a polymer and optionally a surfactant, and a DPP-4 inhibitor such as sitagliptin or a pharmaceutically acceptable salt thereof such as, sitagliptin phosphate. Sitagliptin phosphate having structural formula I below is the dihydrogenphosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

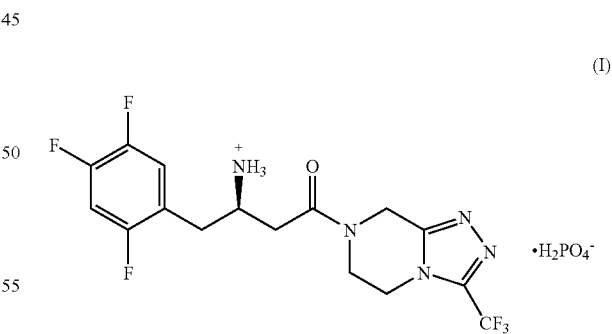

(I)

In one embodiment sitagliptin phosphate is in the form of a crystalline monohydrate. Sitagliptin free base and pharmaceutically acceptable salts thereof are disclosed in U.S. Pat. No. 6,699,871, the contents of which are hereby incorporated by reference in their entirety. Crystalline sitagliptin phosphate monohydrate is disclosed in U.S. Pat. No. 7,326,708, the contents of which are hereby incorporated by reference in their entirety. Sitagliptin phosphate has been approved for marketing in several countries, including the U.S., Europe, Canada, and Mexico, for the treatment of Type 2 diabetes and is branded as JANUVIA® in the U.S. and elsewhere. For reviews, see D. Drucker, et al., "Sitagliptin," *Nature Reviews Drug Discovery*, 6: 109-110 (2007); C. F. Deacon, "Dipeptidyl peptidase 4 inhibition with sitagliptin: a new therapy for Type 2 diabetes," *Exp. Opin. Invest. Drugs*, 16: 533-545 (2007); K. A. Lyseng-Williamson, "Sitagliptin," *Drugs*, 67: 587-597 (2007); and B. Gallwitz, "Sitagliptin: Profile of a Novel DPP-4 Inhibitor for the Treatment of Type 2 Diabetes (Update)," *Drugs of Today*, 43: 801-814 (2007).

In certain embodiments, the pharmaceutical formulations described herein include taranabant and sitagliptin phosphate wherein such pharmaceutical formulations are formed into solid, oral dosage forms such as tablet, capsules or caplets. In such embodiments such formulations contain from 0.01 to 1,000 mg, particularly 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of each therapeutic agent, or therapeutic agents thereof. For example in certain embodiments, the solid, oral pharmaceutical dosage form contains between 0.5 mg to 6 mg of taranabant and 50 mg to 200 mg of sitagliptin free base anhydrate.

Processes of Making Pharmaceutical Formulations

Also described herein are methods of making pharmaceutical dosage forms that include a CB-1 inverse agonist and a polymer. More specifically, described herein are methods of making pharmaceutical formulations that include solid dispersions that include a CB-1 inverse agonist, such as taranabant, and a polymer.

In certain embodiments, the solid dispersions that are included in the pharmaceutical formulations described herein are extruded. In certain embodiments, the solid dispersions described herein are made by the method of hot-melt extrusion. Other methods of forming solid dispersions include mechanical activation and spray-drying techniques.

Pre-Extrusion Process

Prior to being extruded, in certain embodiments, the formulation components to be extruded can be put through one or more pre-extrusion processes. During the pre-extrusion process formulation components are pre-mixed prior to being added to the extruder. For example, the polymer and the therapeutic agent can be combined in a high shear granulator over a period of several minutes. After the polymer and therapeutic agent have been sufficiently combined a surfactant or a combination of surfactants can be added to the polymer and the therapeutic agent. The surfactant can be added slowly over period of several minutes. Once the surfactant is added the polymer/therapeutic agent/surfactant mixture can be further blended for several minutes. Tumble blenders or high shear mixers can be used to mix the formulation components.

The pre-extrusion process is optional and may not be needed in the case where the individual components can be fed into the extruder via gravimetric or volumetric powder feeders and liquid nozzles.

Extrusion Process

In certain embodiments the solid dispersion described herein are made using hot-melt extrusion (HME). HME offers many advantages over traditional pharmaceutical processing techniques such as, 1) eliminates or greatly reduces the amount of solvents or water needed during the manufacturing process; 2) eliminates processing steps such as time-consuming drying steps; 3) offers possible improvement of the bioavailability of the therapeutic agent through the creation of a solid dispersion of the therapeutic agent.

Hot-melt extrusion equipment usually consists of an extruder, downstream auxiliary equipment, and monitoring tools. Extruders typically include a feeding hopper, barrel, screw(s), die, screw driving unit, and a heating/cooling device. To process the pharmaceutical formulations described herein, any type of extruder may be used so long as the extruder is capable of producing a solid dispersion. In certain embodiments, the solid dispersions described herein were extruded in co-rotating, twin screw extruders equipped with twin screw powder feeders operating in either volumetric or gravimetric mode.

Downstream equipment is used generally to cool and collect the extrudate prior to further processing. Different types of downstream processing equipment can be used during the hot-melt extrusion process. For example, to cool the extrudate, chill rolls, cooling baths, or cooling air tunnels using either ambient or chilled air can be used. Once the extrudate is chilled or during the chilling process, the extrudate can be cut into granules by a pelletizer or otherwise ground down in to smaller particles for further processing.

In addition to cooling and collecting, downstream equipment can be used to directly shape the extrudate into a final dosage form. The extrudate could also be directly shaped into final dosage forms by either injection molding, calendaring, or other shaping processes.

Monitoring tools can include temperature gauges, screw speed controllers, extrusion torque monitors, and pressure gauges. Such tools are used for performance and product quality evaluation.

The die is attached to the end of the barrel. The geometrical design of the die will control the physical shape of the molten extrudate. For example, the geometrical design of the die can include a single circle, square, rectangle, triangle, slit or other geometric-shaped hole or a series of circle, square, rectangle, triangle, slit or other geometric-shaped holes. In certain embodiments the dies used during the extrusion process have a 3mm diameter single circular hole or 4×3mm diameter circular holes. The die temperature can range between 120-180° C. and have a die pressure of 0-40 bar.

Hot-melt extrusion processing conditions such as feed rate, screw speed and barrel temperature can vary greatly, depending on the materials being extruded. For example, processing conditions can depend on the chemical stability and physical properties of the therapeutic agent and/or polymer being extruded. Such properties include the molecular weight, glass transition temperature, and the melting point of either the therapeutic agent and/or polymer. Additionally, in order to improve the stability of the therapeutic agent or polymer during the extrusion process, plasticizers, antioxidants, and other additives can be included in the formulation.

The minimum extruder screw speed should be sufficient to convey all the material from the feeding hopper to the extruder barrel while allowing the extruder to run at acceptable torque levels. In certain embodiments, the screw speed can be between 90 to 600 rpm. For example the screw speed can be between 150-600 rpm or 90-360 rpm. For example, the screw speed can be about 90, 100, 110, 120, 130, 140, 150, 160, 170, 180, 190, 200, 210, 220, 230, 240, 250, 260, 270, 280, 290, 300, 310, 320, 330, 340, 350 or 360.

The barrel temperature can include a range of temperatures. The barrel temperature range should be able to produce the desired solid dispersion without compromising the integrity of the therapeutic agent and polymer. In certain embodiments, the barrel temperature range can range between 20-145° C. In other embodiments the barrel temperature range can range between 25-165° C. In still other embodiments the barrel temperature range can be between 25-180° C. Ideally, the temperature of the melting section of the extruder is normally set at 20-100° C. above the glass transition temperature of the solid dispersion.

In certain embodiments, the feed rate can range between 0.2-10 kg/hr. In other embodiments the feed range can range between 0.5-1.44 kg/hr. In still other embodiments the feed rate can be between 2-5.34 kg/hr.

Methods of Treatment

The pharmaceutical formulations described herein are useful for the treatment, control, or prevention of obesity. Obesity may be due to any cause, whether genetic or environmental.

The pharmaceutical formulations described herein are also useful for the treatment, control, or prevention of Type 2 diabetes.

The pharmaceutical formulations described herein are also useful for the treatment, control, or prevention of conditions associated with obesity. The conditions associated with obesity include conditions caused by, or result from obesity. Examples of conditions associated with obesity include, but are not limited to, diabetes including Type 1 diabetes or Type 2 diabetes. Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin.

Other conditions associated with obesity include gestational diabetes mellitus and prediabetic conditions such as, elevated plasma insulin concentrations, impaired glucose tolerance, impaired fasting glucose and insulin resistance syndrome. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Additional conditions associated with obesity include, but are not limited to overeating, binge eating, and bulimia, hypertension, dyslipidemia, hyperlipidemia, endometrial, breast, prostate, kidney and colon cancer, osteoarthritis, obstructive sleep apnea, gallstones, heart disease, abnormal heart rhythms and arrythmias, myocardial infarction, congestive heart failure, coronary heart disease, sudden death, stroke, polycystic ovarian syndrome, craniopharyngioma, Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

Further examples of obesity-related disorders are Metabolic Syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, lower back pain, gallbladder disease, hyperuricemia, gout, and kidney cancer, and increased anesthetic risk. The compositions of the present invention are also useful to treat Alzheimer's disease and smoking.

Methods of treating or preventing obesity and any additional conditions associated with obesity include administering to a patient in need thereof a pharmaceutical formulation as described herein. A subject in need thereof is an obese subject. In another embodiment, a subject in need thereof is an obese subject with diabetes. In another embodiment, a subject in need thereof is an obese subject at risk of developing diabetes. In another embodiment, a subject in need thereof is an obese diabetic subject. In another embodiment, a subject in need thereof is a diabetic subject at risk of developing obesity.

In another embodiment, a subject in need thereof is an obese subject with cardiac hypertrophy, or left ventricular hypertrophy. In another embodiment, a subject in need thereof is an obese diabetic subject with cardiac hypertrophy, or left ventricular hypertrophy. In another embodiment, a subject in need thereof is an obese subject at risk of developing cardiac hypertrophy, or left ventricular hypertrophy. In another embodiment, a subject in need thereof is an obese diabetic subject at risk of developing cardiac hypertrophy, or left ventricular hypertrophy. In another embodiment, a subject in need thereof is an obese diabetic subject with cardiac hypertrophy, or left ventricular hypertrophy, undergoing PPARγ agonist treatment. In another embodiment, a subject in need thereof is an obese diabetic subject undergoing PPARγ agonist treatment and at risk of developing cardiac hypertrophy, or left ventricular hypertrophy In still another embodiment a subject in need thereof is an obese subject with Metabolic Syndrome. In another embodiment, a subject in need thereof is an obese subject at risk of developing Metabolic Syndrome. In another embodiment, a subject in need thereof is a diabetic subject with Metabolic Syndrome. In another embodiment, a subject in need thereof is an obese diabetic subject with Metabolic Syndrome. In another embodiment, a subject in need thereof is an obese subject at risk of developing Metabolic Syndrome. In another embodiment, a subject in need thereof is an obese diabetic subject at risk of developing Metabolic Syndrome. In another embodiment, a subject in need thereof is an obese subject with Metabolic Syndrome. In another embodiment, a subject in need thereof is an obese subject at risk of developing Metabolic Syndrome. In another embodiment, a subject in need thereof is a diabetic subject with Metabolic Syndrome. In another embodiment, a subject in need thereof is an obese diabetic subject with Metabolic Syndrome. In another embodiment, a subject in need thereof is an obese subject at risk of developing Metabolic Syndrome. In another embodiment, a subject in need thereof is an obese diabetic subject at risk of developing Metabolic Syndrome.

Methods of treating or preventing obesity and conditions associated with obesity refer to the administration of the pharmaceutical formulations described herein to reduce or maintain the body weight of an obese subject or to reduce or maintain the body weight of an individual at risk of becoming obese. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy and preventing weight gain from cessation of smoking. Another outcome of treatment may be decreasing the occurrence of and/or the severity of obesity-related diseases. Yet another outcome of treatment may be decreasing the risk of developing diabetes in an overweight or obese subject. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the pharmaceutical formulations described herein to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The pharmaceutical formulations described herein are useful to the treatment of an obese individual with atherosclerosis or at risk of developing atherosclerosis. Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis. The pharmaceutical formulations that include a DPP-4 inhibitor in combination with a cannabinoid CB-1 receptor antagonist/inverse agonist may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. An atherosclerotic disease event encompasses coronary heart disease events, cerebrovascular events, and intermittent claudication. It is intended that persons who have previously experienced one or more non-fatal atherosclerotic disease events are those for whom the potential for recurrence of such an event exists.

The pharmaceutical formulations described herein can be administered to a patient in need thereof, once a day or multiple times a day so long as the recommended daily dosage of the CB-1 inverse against and the additional therapeutic agent, such as a DPP-4 inhibitor is reached. In certain embodiments, the pharmaceutical dosage forms described herein are once-a-day solid tablets, capsules or caplets. In certain embodiments, the pharmaceutical dosage forms described herein are twice-a-day solid tablets, capsules or caplets.

EXAMPLES

The following examples are provided to more fully illustrate the invention and are not to be construed as limiting the scope of the invention, which is defined by the appended claims.

Example 1

Listed in Table 1 are solid dispersion formulations that were extruded.

TABLE 1

| Formulation No. | 1 | 2 | 3 | 4 | 5 | 6 | 7 | 8 |
|---|---|---|---|---|---|---|---|---|
| Taranabant | 10% | 10% | 10% | 10% | 10% | 10% | 10% | 10% |
| Polysorbate 80 | 1.5% | 1.5% | 0% | 1.5% | 1.5% | 0% | 0% | 3% |
| Sorbitan Monoleate | 1.5% | 1.5% | 2.5% | 1.5% | 1.5% | 0% | 0% | 3% |
| Vitamin E TPGS | 0% | 0% | 2.5% | 0% | 0% | 5% | 10% | 0% |
| PVP | 0% | 0% | 0% | 10% | 20% | 0% | 0% | 0% |
| Kollidon VA64 | 87% | 86.17% | 85% | 77% | 67% | 85% | 80% | 84% |
| BHA | 0% | 0.83% | 0% | 0% | 0% | 0% | 0% | 0% |

Pre-Extrusion Processing

If applicable, combinations of surfactants were first mixed using a mixer until a homogeneous solution was obtained. In a high shear granulator, polymer and taranabant were blended for 3-5 minutes using 300 rpm impeller speed. The surfactant or surfactant mixture was then added to the granulator over a period of 3-8 minutes with an impeller speed of 300 rpm and a chopper speed of 1000 rpm. After the addition of the surfactant, the mixture was further blended for 5 minutes.

Extrusion 16-mm ThermoElectron or 27-mm Leistritz co-rotating extruders were used, depending on the processing scale. The design for both of the extruders included a powder feed hopper that conveyed material into the extruder barrel. The first mixing zone included a series of 30, 60 and 90 degree offset mixing elements. From the first mixing zone the material was conveyed to a second mixing zone which included a series of 30, 60 and 90 degree offset mixing elements. From the second mixing zone the material was conveyed to a die block. A short metering section of lower free volume forward conveying elements was located before the die block to produce a consistent pressure and flow rate at the die. Table 2 shows the conditions that were used to process Formulations 1-8.

TABLE 2

| Formulation | Extruder | Screw Speed | Feed Rate | Barrel Temp. Range (° C.) | Die |
|---|---|---|---|---|---|
| Formulation 1 | 16-mm Extruder | 150-600 rpm | 0.6-1.44 kg/hr | 25-180 | Single hole with 3 mm diameter |
| Formulation 1 | 27-mm Extruder | 90-360 rpm | 2.22-5.35 kg/hr | 25-165 | 4 × 3-mm holes |

TABLE 2-continued

| Formulation | Extruder | Screw Speed | Feed Rate | Barrel Temp. Range (° C.) | Die |
|---|---|---|---|---|---|
| Formulation 2 | 16-mm Extruder | 150 rpm | 10-20% | 130-160 | Single hole with 3 mm diameter |
| Formulation 3 | 16-mm Extruder | 150 rpm | 10-20% | 130-160 | Single hole with 3 mm diameter |
| Formulation 4 | 16-mm Extruder | 150 rpm | 10-20% | 130-160 | Single hole with 3 mm diameter |
| Formulation 5 | 16-mm Extruder | 150 rpm | 10-20% | 130-160 | Single hole with 3 mm diameter |
| Formulation 6 | 16-mm Extruder | 150 rpm | 10-20% | 130-160 | Single hole with 3 mm diameter |
| Formulation 7 | 16-mm Extruder | 75-80 rpm | 10-20% | 110-130 | Single hole with 3 mm diameter |
| Formulation 8 | 16-mm Extruder | 75-80 rpm | 10-20% | 110-130 | Single hole with 3 mm diameter |

The resulting extrudate was cooled using ambient or chilled air cooling on a conveyor belt or using a chilled roll assembly. The cooled extrudate was then milled.

Physical Characterization

Table 3 lists the physical characteristics of Formulations 1 and 6 of Table 1.

TABLE 3

| | Formulation No. | | | | | |
|---|---|---|---|---|---|---|
| | 1 | | | 6 | | |
| Dry Tg | 90° C. | | | 85° C. | | |
| Crystalinity-XRPD | Amorphous | | | Amorphous | | |
| Crystalinity-Microscopy | Amorphous | | | Amorphous | | |
| | 10 min | 30 min | 60 min | 10 min | 30 min | 60 min |
| Dissolution Profile | 74.9% | 90.8% | 87.8% | 86.8% | 88.4% | 84.3% |

Example 2

In vivo Studies

Pharmacokinetic studies were performed in monkeys, comparing dry filled capsules of Formulation 1 and liquid filled capsules (LFC) containing taranabant in a Imwitor/Tween carrier.

Bioavailability was determined in vivo by dosing trial formulations and/or other formulations of taranabant only, to Rhesus monkeys (n=6, full crossover) at a dose of about 0.6 mg/kg, assuming a 10 kg monkey, of the taranabant and then measuring the amount of taranabant in the serum or blood as a function of time. Comparisons were made with other formulations containing the same amount and same concentration of taranabant, such as a solid formulation with conventional excipients or a liquid filled gelatin capsule containing equal parts by weight of Tween 80 and Imwitor. The summary of mean pharmacokinetic parameters for the three capsule formulations is shown in Table 4.

TABLE 4

| Formulation | Doses (mg) | $AUC_{0-24\,hr}$ ($\mu M * hr$) | $C_{MAX}$ ($\mu M$) | $T_{MAX}$ (hr) | Ratio |
|---|---|---|---|---|---|
| Formulation A (LFC: Taranabant/Imwitor/Tween) | 6 (n = 6) | 2.16 ± 0.28 | 0.409 ± 0.05 | 1.75 ± 0.51 | 1 |
| Formulation B Tablet: Formulation 1 (16 mm Extrusion) | 6 (n = 6) | 2.65 ± 0.0.47 | 0.292 ± 0.07 | 4.33 ± 0.33 | 1.23 |

FIG. 1 shows cyclic differential scanning calorimetry (DSC) of extrudate sample of Formula 1 from the 16 mm extruder spanning a range of screw speeds and feed rates with varying degrees of mechanical energy imparted on the material (low energy: 1.44 kg/hr, 150 rpm, normal energy: 1.02 kr/hr, 200 rpm, high energy: 0.6 kg/hr, 600rpm). The results in FIG. 1 show no crystalline peaks and the presence of a single glass transition temperature around 90° C.

Figure 2:
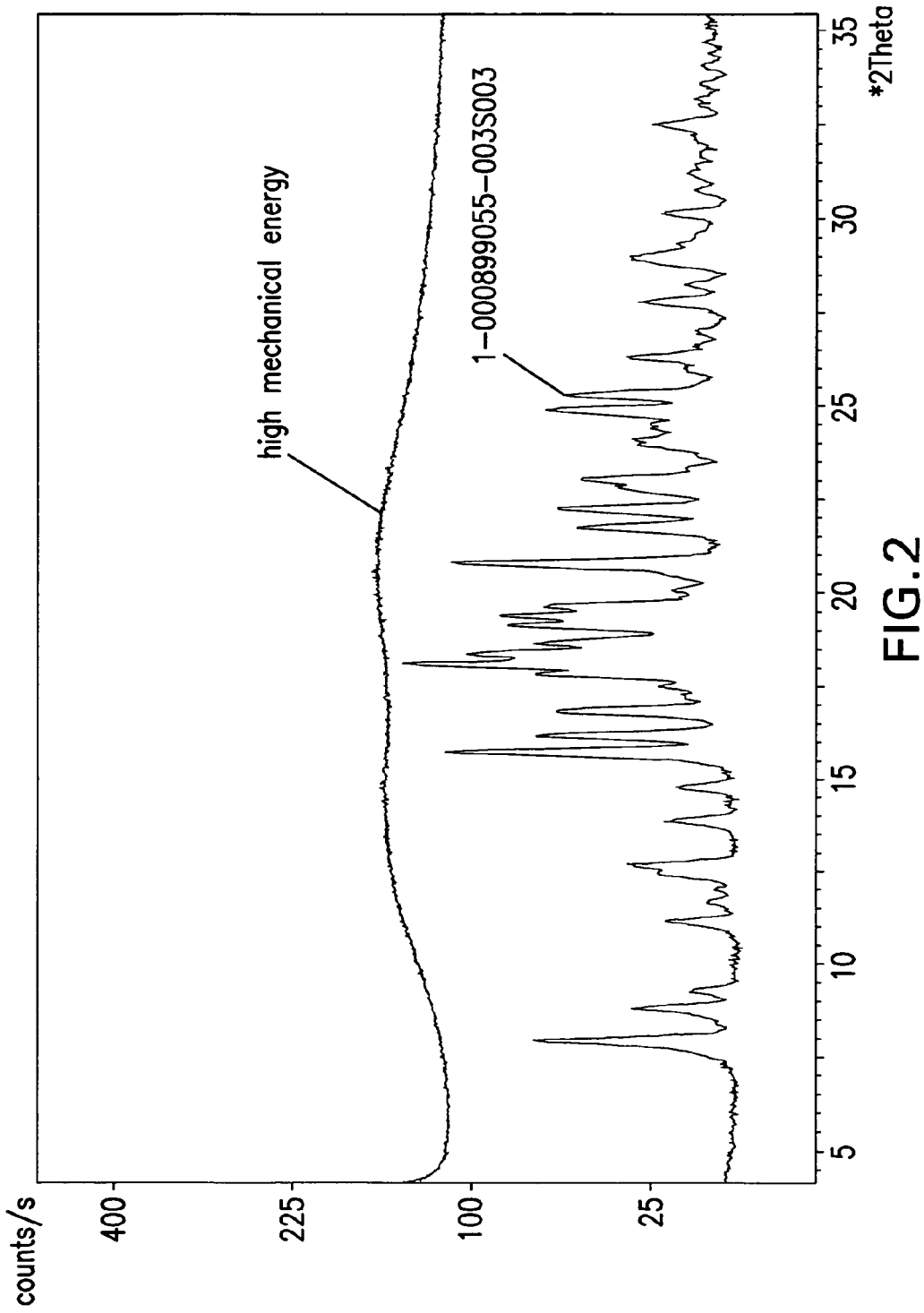
FIG. 2 shows X-ray powder diffraction on ground up extrudate of Formula 1 of Example 1 from the 16 mm extruder.

FIG. 2 shows X-ray powder diffraction on ground up extrudate of Formula 1 from the 16 mm extruder spanning a range of screw speeds and feed rates with varying degrees of mechanical energy imparted on the material (low energy: 1.44 kg/hr, 150 rpm, normal energy: 1.02 kr/hr, 200 rpm, high energy: 0.6 kg/hr, 600 rpm).

Tablets containing a pharmaceutical formulation encompassed by the present application exhibit an area under the concentration versus time curve (AUC) that is greater than that of formulations without the concentration-enhancing polymer. The area under the concentration versus time curve (AUC) is 1.23 times greater than that of the LFCs. The pharmaceutical formulations described herein exhibit improved in vivo bioavailability of taranabant compared with formulations that do not have the concentration-enhancing polymer.

Example 3

Tablets: Roller Compaction Process

The milled particles of extruded Formula I containing taranabant and PVP-PVA were blended with sitagliptin, microcrystalline cellulose, dibasic calcium phosphate, and croscarmellose sodium in the amounts shown in Table 5, using a V- or bin blender.

TABLE 5

| Ingredient (mg/unit) | 100 mg (sitagliptin free base anhydrate)/2 mg (taranabant) |
|---|---|
| Taranabant | 2.00 |
| PVP-PVA | 46.50 |
| Polysorbate 60 | 0.75 |
| Sorbitan Monooleate | 0.75 |
| Sitagliptin dihydrogenphosphate | 128.50* |
| Microcrystalline cellulose | 98.75 |
| Dibasic calcium phosphate, anhydrous | 98.75 |
| Croscarmellose sodium | 8.00 |
| Magnesium stearate | 4.00 |
| Sodium strearyl fumarate | 12.00 |
| CORE TABLET WEIGHT | 400 |
| Film coat blend, powder | 10 |
| COATED TABLET WEIGHT | 410 |

*Equivalent to 100 mg of sitagliptin free base anhydrate.

The blend was then lubricated with magnesium stearate and sodium stearyl fumarate in the same blender. The lubricated blend was roller compacted using TFC-Labo roller compactor and milled using rotary fine granulators. The milled granules were lubricated with magnesium stearate and sodium stearyl fumarate in a V- or bin blender and compressed into tablets. The tablets were then coated with a non functional coating for product differentiation and taste masking.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein by reference, in their entirety, for all purposes related to this disclosure.

While the invention has been shown and described herein with reference to particular embodiments, it is to be understood that the various additions, substitutions, or modifications of form, structure, arrangement, proportions, materials, and components, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. A pharmaceutical formulation comprising a solid dispersion made by hot-melt extrusion comprising a cannabinoid receptor inverse agonist having formula I:

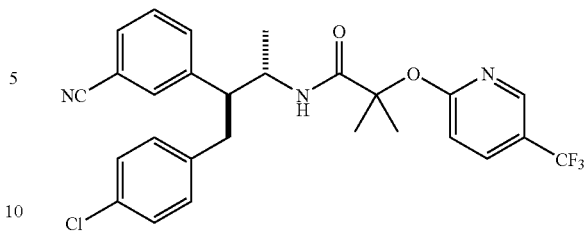

and a concentration-enhancing polymer selected from the group consisting of polyvinylpyrrolidinone, and polyvinylpyrrolidinone-polyvinylacetate copolymers, wherein the concentration-enhancing polymer comprises 80%-95% of the solid dispersion by weight.

2. The pharmaceutical formulation of claim 1, wherein the solid dispersion further comprises a surfactant.

3. The solid dispersion of claim 2, wherein the surfactant is selected from the group consisting of anionic surfactants and nonionic surfactants.

4. The solid dispersion of claim 2, wherein the surfactant is selected from the group consisting of sodium dodecyl sulphate, sorbitan fatty acid esters, polyoxyethylene sorbitan fatty acid esters, polyoxyethylene castor oils, polyoxyethylene hydrogenated castor oils, vitamin E TPGS; and mixtures thereof.

5. The solid dispersion of claim 1, wherein the cannabinoid receptor inverse agonist comprises 5%, 10% or 20% of the solid dispersion by weight.

6. The pharmaceutical formulation of claim 1 further comprising an additional therapeutic agent.

7. The pharmaceutical formulation of claim 6, wherein the additional therapeutic agent is a dipeptidyl peptidase-IV inhibitor.

8. The pharmaceutical formulation of claim 7, wherein the dipeptidyl peptidase-IV inhibitor is sitagliptin or a pharmaceutically acceptable salt thereof.

9. The pharmaceutical formulation of claim 7, wherein the dipeptidyl peptidase-IV inhibitor is sitagliptin dihydrogenphosphate.

10. The pharmaceutical formulation of claim 1, wherein the dosage form contains 0.5 mg to 6 mg of the cannabinoid receptor inverse agonist.

11. The pharmaceutical formulation of claim 1, wherein the dosage form contains 25 mg to 200 mg of the dipeptidyl peptidase-IV inhibitor.

12. The pharmaceutical formulation of claim 1, wherein the pharmaceutical formulation is a tablet or caplet.

13. A method of treating obesity comprising administering to a patient in need thereof a pharmaceutical formulation of claim 1.

14. The method of claim 13, wherein the pharmaceutical formulation further comprises a surfactant.

15. The method of claim 13, wherein the pharmaceutical formulation is in the form of a tablet.

* * * * *